United States Patent [19]
Teng

[11] Patent Number: 5,720,611
[45] Date of Patent: Feb. 24, 1998

[54] LONG-ARMED TYPE UPRIGHTING SPRING FOR MOLAR TOOTH

[76] Inventor: Chi-Ming Teng, 4Fl., #342,SEC. 1 Keelung Rd., Taipei, Taiwan

[21] Appl. No.: 563,919

[22] Filed: Nov. 29, 1995

[51] Int. Cl.$^6$ ................................................. A61C 7/12
[52] U.S. Cl. ......................................................... 433/21
[58] Field of Search ...................................... 433/18, 21

[56] References Cited

U.S. PATENT DOCUMENTS

| | | | |
|---|---|---|---|
| 4,292,025 | 9/1981 | Forster | 433/18 |
| 4,856,992 | 8/1989 | Bergersen | 433/18 |
| 5,163,839 | 11/1992 | Metcalf | 433/6 |
| 5,246,366 | 9/1993 | Tracey | 433/21 |
| 5,302,117 | 4/1994 | Kraut et al. | 433/18 |
| 5,443,284 | 8/1995 | Franseen et al. | 433/18 |

FOREIGN PATENT DOCUMENTS 595207  3/1934  Germany .................. 433/18

*Primary Examiner*—Cary E. O'Connor
*Attorney, Agent, or Firm*—W. Wayne Liauh

[57] ABSTRACT

A long-armed type molar uprighting spring is disclosed. It contains: (a) a lingual groove rest for mounting the uprighting spring in a lingual groove of a first molar; (b) a loop, which extends from the lingual groove and can be fixedly mounted around a mesial side of a second molar; (c) a buccal bracket rest extending from one end of the loop opposing the lingual groove rest for resting the upright spring on a buccal bracket of the first molar; (d) a reactivating area, which extends from the other end of the buccal bracket rest to fit into an area between the first molar and a second premolar so as to provide a stronger activating function; (e) a lever arm, which extends from the reactivating area to provide an uprighting function in accordance with impacted condition of the second molar. The long-armed type uprighting spring is specially designed in accordance with a first kind lever theory so as to overcome the problem of poor bonding that may affect a molar. After the uprighting spring is mounted between molars, an impacted molar will become uprighted so as to grow continuously to a precise position and the patient will be provided with a perfect orthodontic result within several weeks.

1 Claim, 11 Drawing Sheets

:::page-number
1
:::

LONG-ARMED TYPE UPRIGHTING SPRING FOR MOLAR TOOTH

BACKGROUND OF THE INVENTION

There are about 3% of people having an ectopic impacted first molar on the upper jaw. Some people have an ectopic impacted second molar on the mandible. The reason is that, when a patient is under orthodontic treatment, the first molar on the mandible could incline backwards as a result of the anchorage preparation, or of the morphology of the first molar itself, or of the insufficient length of the dental arch; consequently, the second molar would be affected to have an ectopic impacted condition.

Conventionally, an inclined molar will, if not serious, be mounted with a brass wire to have the molar move gradually towards the distal side, or be uprighted with an elevator. As the dental technique has been developed rapidly with each pass day, a steel wire or a band is used for uprighting a molar.

During clinical orthodontic treatment, an erupting and impacted molar often causes damage to the gum tissue; an irregular dentition causes the dental arch not perfect; further, such an impacted molar would cause a poor-bonding result to an orthodontic bracket; moreover, the band is rather difficult to mount on the impacted molar.

SUMMARY OF THE INVENTION

This invention relates to a long-armed type molar uprighting spring made of a stainless steel wire, and it is designed in accordance with the first kind lever theory; the present invention can overcome the poor result of a bracket bonding to the impacted molar. According to the inclined condition thereof, within two to five weeks, and a perfect uprighting result can be expected.

DETAILED DESCRIPTION

Figure 1:
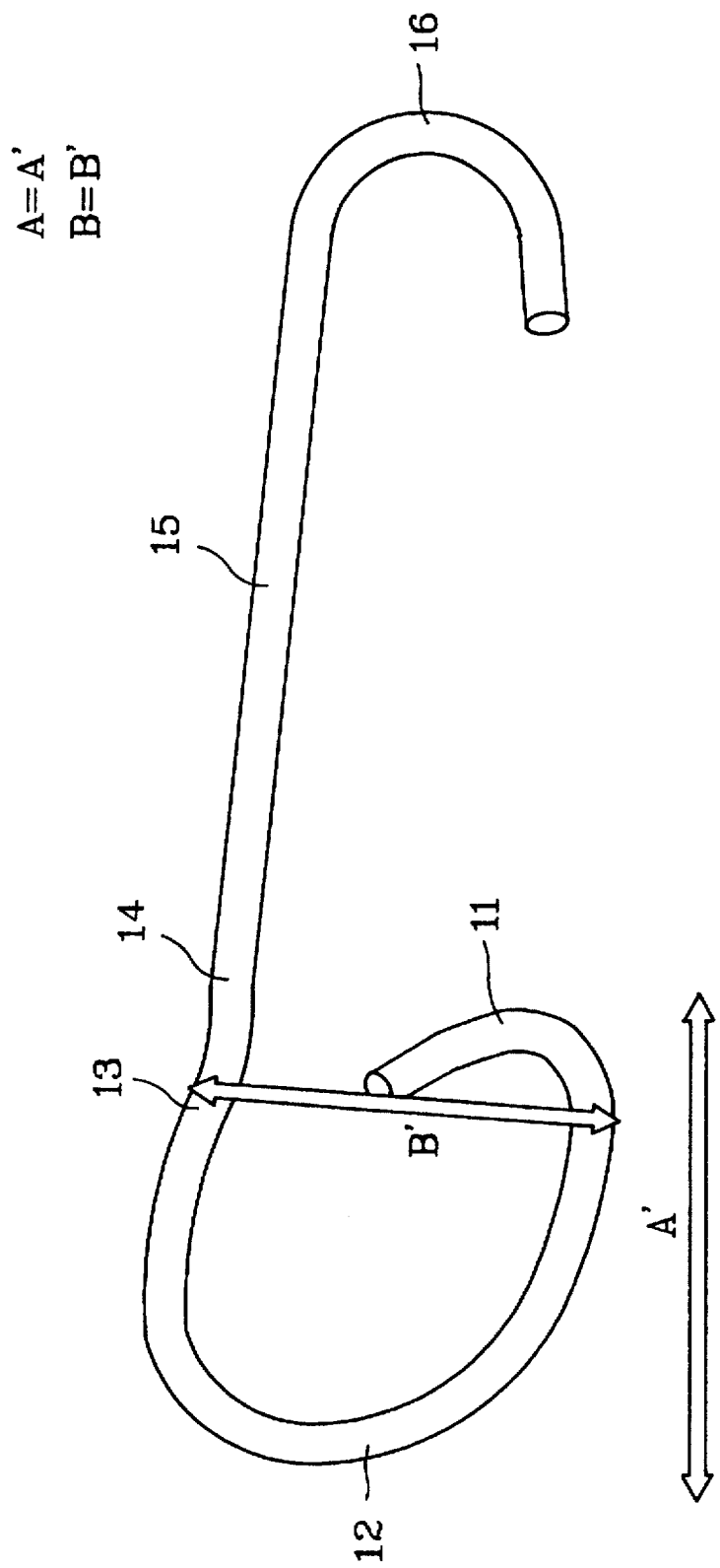
FIG. 1 is a perspective view of an embodiment of a long-armed type uprighting spring according to the present invention.

Referring to FIG. 1, it is a perspective view of a long-armed type uprighting spring 1 according to the present invention; the uprighting spring 1 is made of a stainless steel 22, having different diameters ranging from 0.018, 0.020 and 0.022 inches; the uprighting spring 1 includes: (A) a lingual groove rest 11 formed into a hook to be mounted on the first molar 31 on the lingual groove side, (B) a loop 12 being mounted round the mesial side of the second molar 32, (C) a buccal bracket rest 13 being used to rest the spring 1 on the buccal bracket of the first molar 31, (D) a reactivating area 14, which is an area between the first molar 31 to the second premolar 34, (E) a lever arm 15, which is used for uprighting a given part in accordance with the impacted condition of the second molar, (17) an arc 16, which is a hook bent to penetrate from the lingual part of a contact area: after the arc penetrate the area, the rest part thereof must be cut off.

Figure 2:
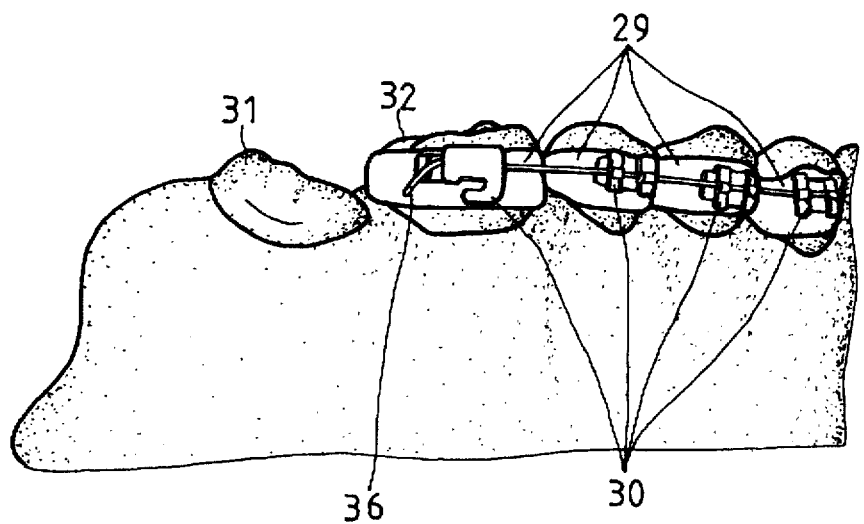
FIG. 2 is a side view of a second molar, of which an impacted part slants forwards.

The uprighting spring 1 of the present invention uses the first kind lever theory to correct the impacted second molar 32, of which the crown nearing the mesial side has become exposed; after orthodontic treatment by using the long-armed type uprighting spring 1 to the serious inclined condition of the second molar 32, and the second time inspect by a dentist by further increasing the gripping force, and following tightening the uprighting spring 1 properly in accordance with the orthodontic treatment condition of the second molar 32, the uprighting spring 1 has become reactivated. At the same time, the following orthodontic material and tools are used, such as a band 29, a bracket 30, and a main wire 36, which are tied together to provide a better anchorage unit as shown in FIG. 2; in this case, side effect caused by the correcting force would reduce to minimum during the time of orthodontic treatment.

Figure 3:
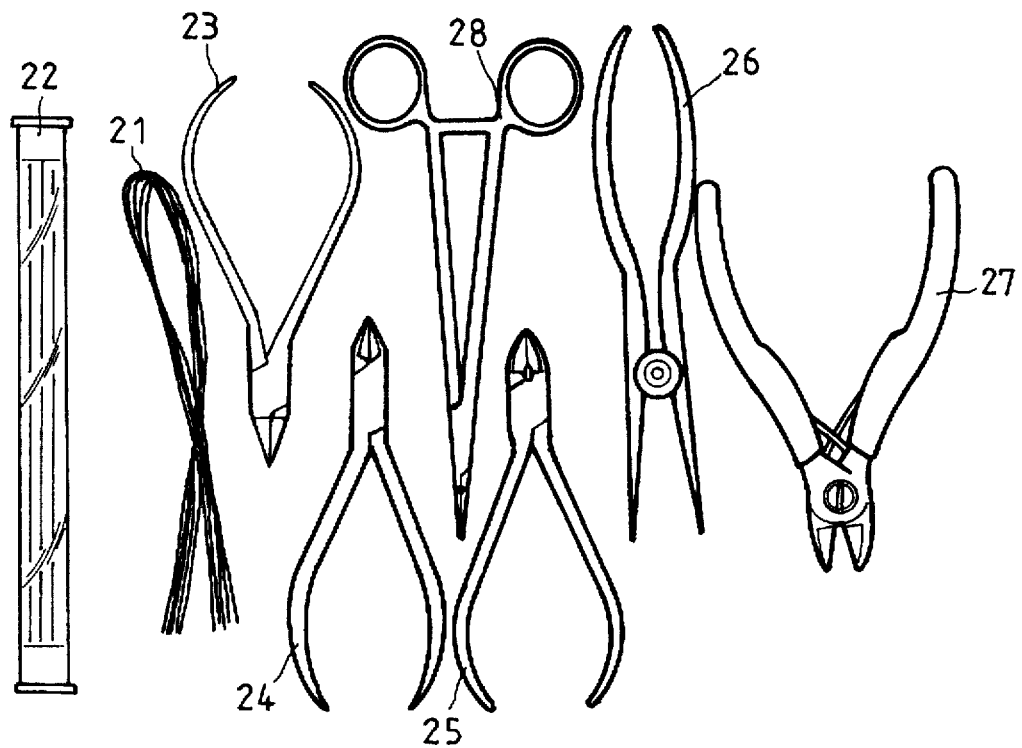
FIG. 3 illustrates materials and tools for correcting a molar according to the present invention.

Before correcting the impacted second molar 32 by using the long-armed type uprighting spring 1, a number of material and tools as shown in FIG. 3 must be prepared, such as:

(a), a ligature wire 21;

(b), a given number stainless steel wires 22 with diameters of 0.018, 0.020 or 0.022 inch;

(c), a pair of loop forming pliers 23;

(d), a bird beak (No. 139) 24 and a light wire cutter 25;

(e), a pair of tying pliers 26;

(f), a heavy cutter 27; and (g), a needle holder 28.

Figure 4:
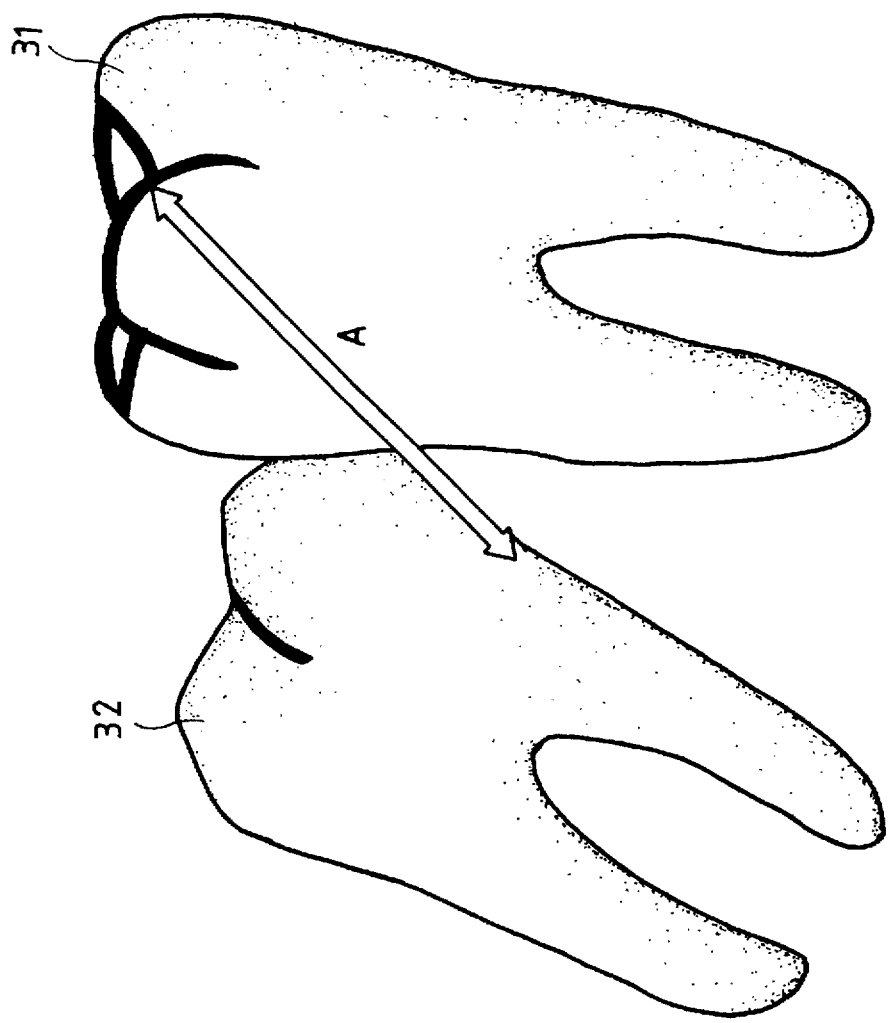
FIG. 4 is a side view of the partial impacted molar.

In order to provide a complete description of the operation steps and structure of the uprighting spring, an embodiment for performing orthodontic treatment to the impacted molar 32 is described as follows:

(1). As shown in a X-ray film, it has been measured a length A (as shown in FIG. 4) from the lingual groove of the first molar 31 to a point under the highest point about 1 mm nearing the mesial side.

Figure 5:
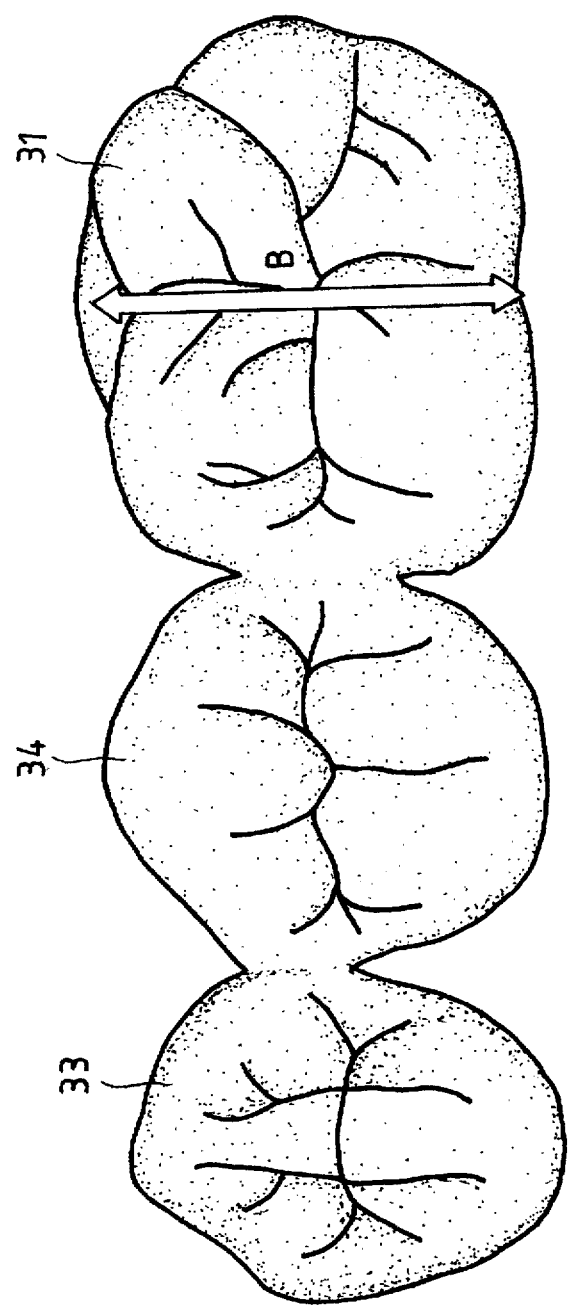
FIG. 5 is a top view of the first molar.

(2). It has been measured a width B (as shown in FIG. 5) from the lingual groove to the buccal side of the first molar 31.

(3). To use No. 139 bird beak 24 to have the steel wire formed into a shape as shown in FIG. 1, in which A' stands for a distance between the most protruding part of the lingual groove rest 11 and the most protruding part of the loop 12;

B' stands for a distance between the starting end of the loop 12 and the buccal bracket rest 13. The stainless steel wire 22 is a bent to a shape of A=A' and B=B'; if A<A', the spring 1 is subject to becoming separated from the contact area soon.

Figure 6:
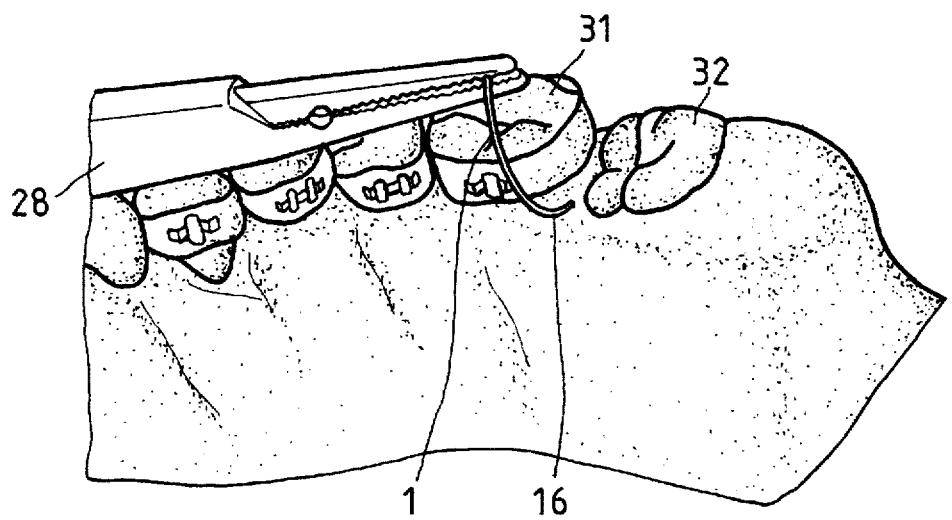
FIG. 6 illustrates a needle holder gripping the front end of an arc spring to insert from the lingual side of the tongue.
Figure 7:
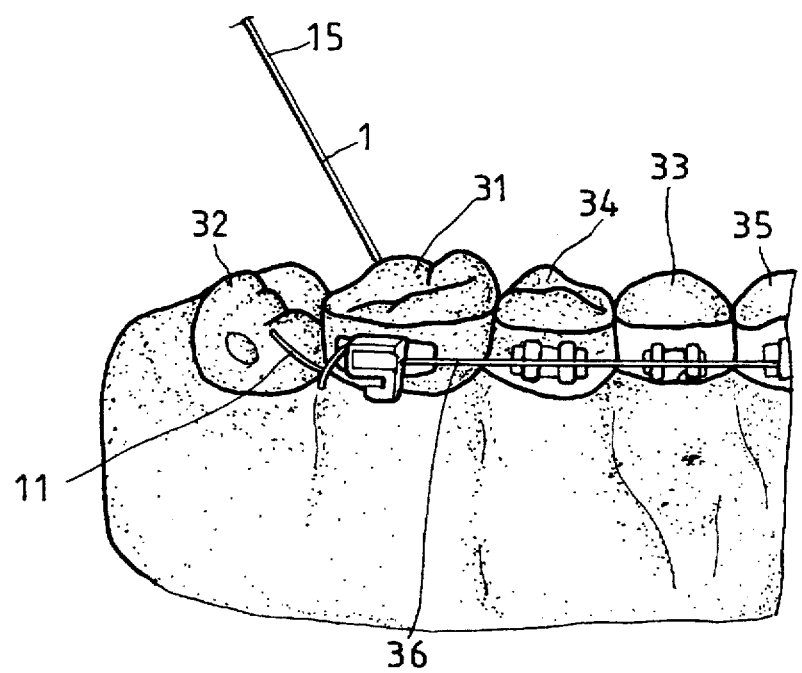
FIG. 7 illustrates an uprighting spring penetrating through the buccal side, and being pulled out with a bird beak No. 139.
Figure 8:
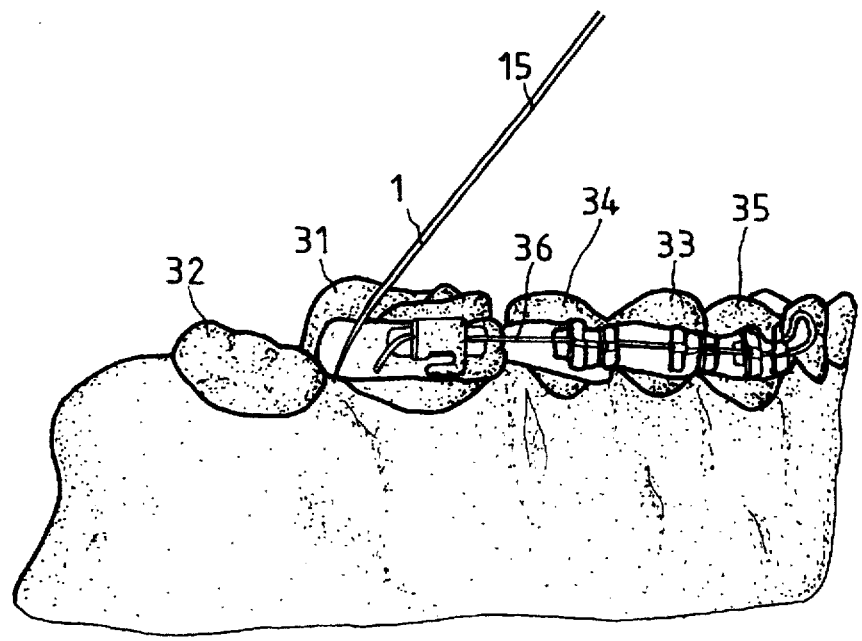
FIG. 8 illustrates a lever arm penetrating through the buccal side.
Figure 9:
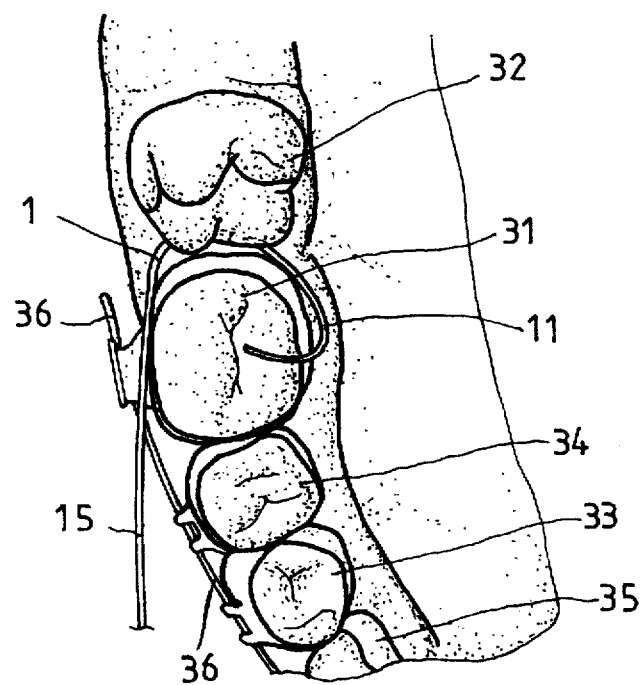
FIG. 9 illustrates a lingual grove rest mounted in place.

(4). Use the needle holder 28 to grip the arc 16 part and to penetrate into the contact area beside the lingual part of the affected part (as shown in FIG. 6); then, the arc 16 will penetrate out of the buccal side (as shown in FIG. 7), and then the lever arm 15 is pulled out with the No. 139 bird beaks 24 and (as shown in FIG. 8); the lingual groove rest 11 of the long-armed type uprighting spring 1 will be mounted on the first molar 31 accurately (as shown in FIG. 9).

Figure 10:
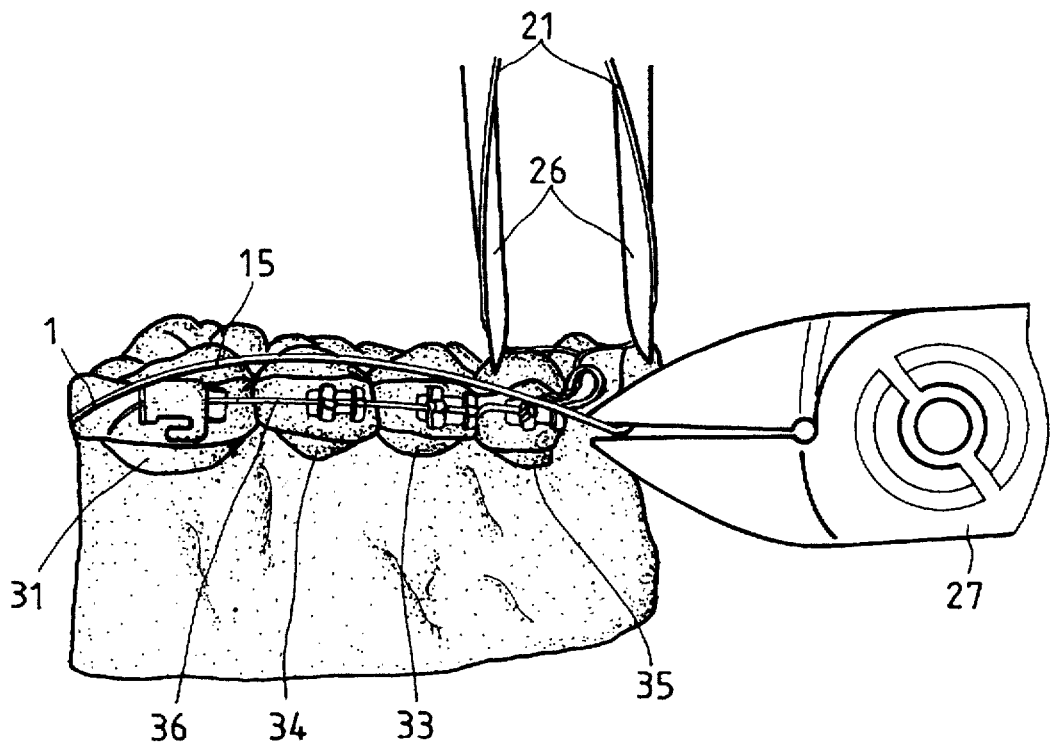
FIG. 10 illustrates a lever arm tied on a canine tooth, and the rest steel wire being cut off.

(5). Tie the lever arm 15 to the bracket of the canine tooth 32, and cut off the rest stainless steel wire 22 (as shown in FIG. 10).

Figure 11:
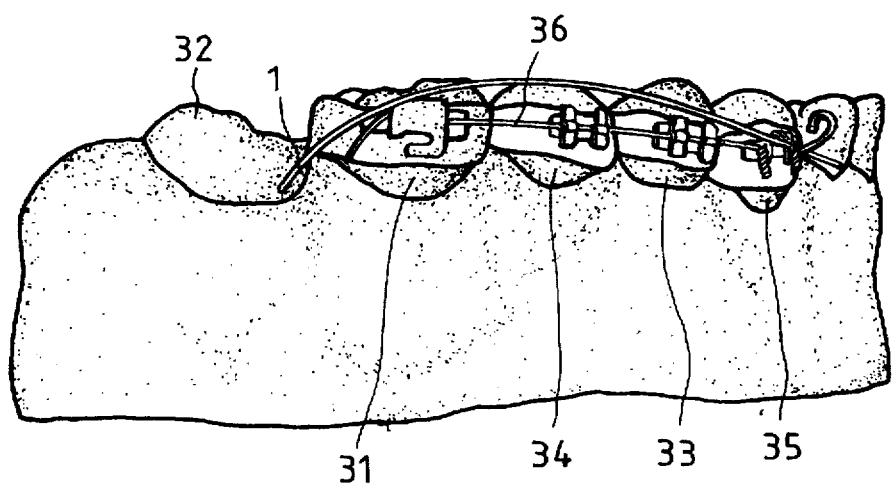
FIG. 11 illustrates an arched part, which is subject to causing occlusal interference.
Figure 12:
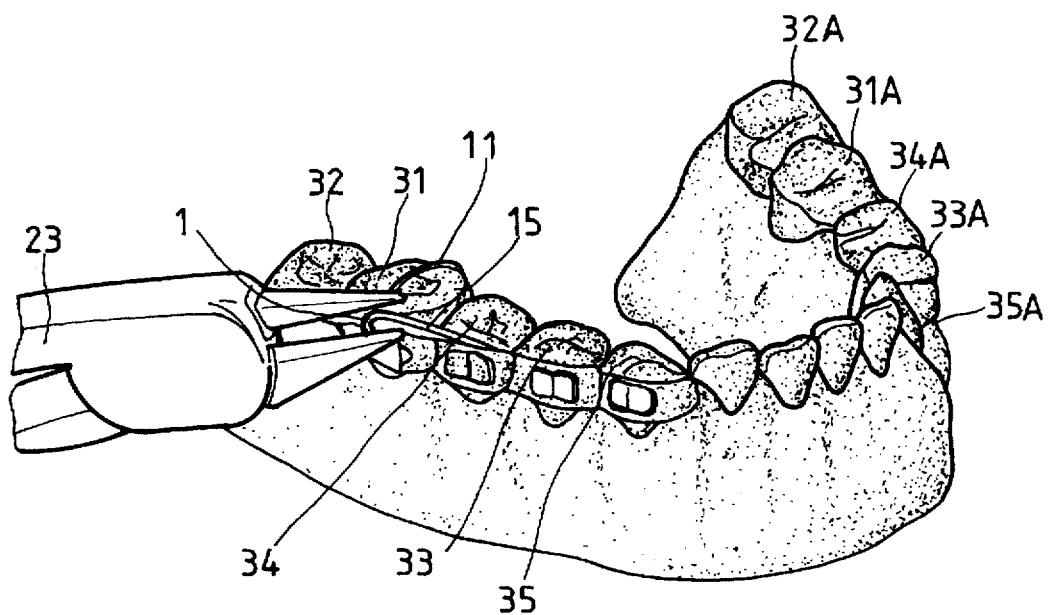
FIG. 12 illustrates using a loop forming pliers to remove the arched part and to activate the uprighting resilient part.
Figure 13:
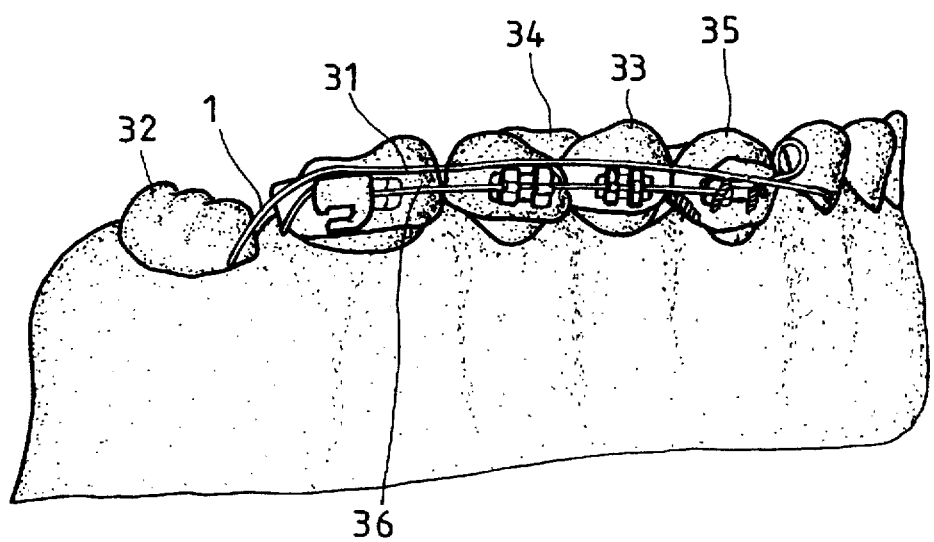
FIG. 13 illustrates the arched part being removed.
Figure 14:
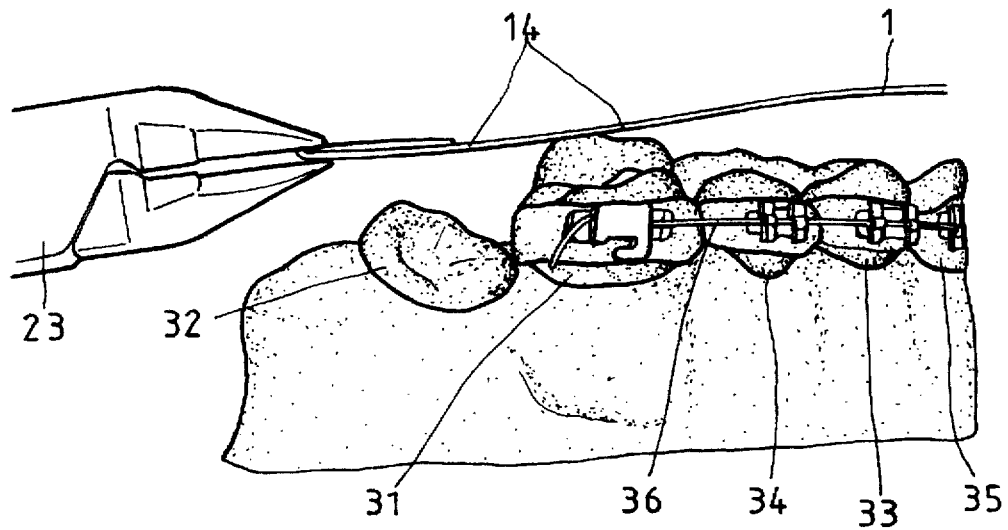
FIG. 14 illustrates a state before activating.
Figure 15:
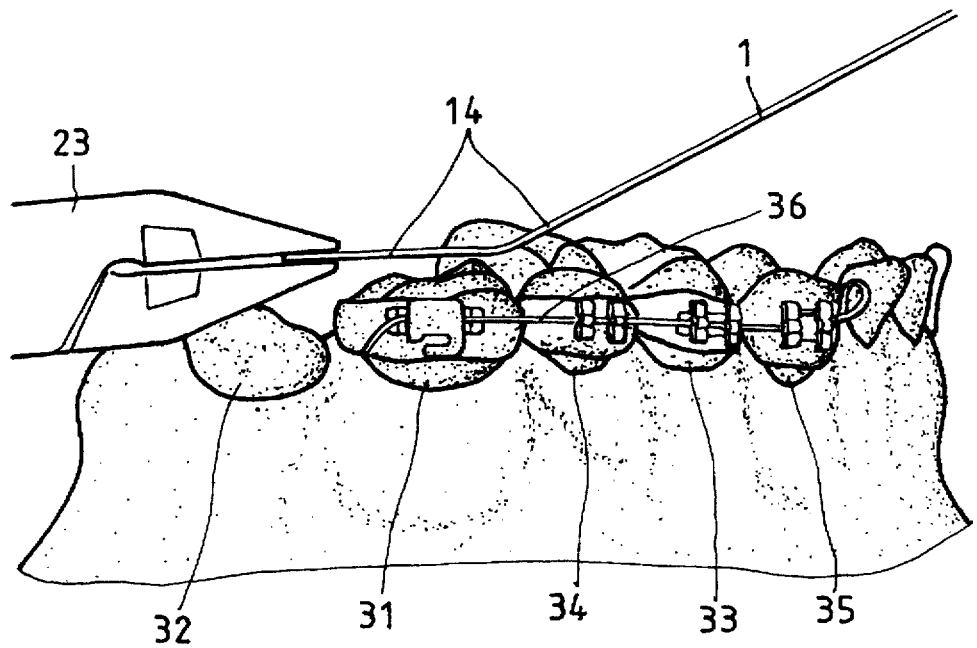
FIG. 15 illustrates a state after activating.

(6). If the steel wire forms an arched part between the first molar 31 and the canine 35, it would cause an occlusal interference to the patient; in that case, the arched part can be removed by means of the loop forming pliers 23 (as shown in FIGS. 11 and 12). FIG. 13 illustrates the arched part of the long-armed type uprighting spring having been removed by using the loop forming pliers 23, and simultaneously the resilient force of the uprighting spring 1 able to have a stronger activating function in the reactivating area 14 in accordance with the required condition of the second molar 32. The conditions before reactivating and after reactivating are shown in FIGS. 14 and 15 respectively.

Figure 16:
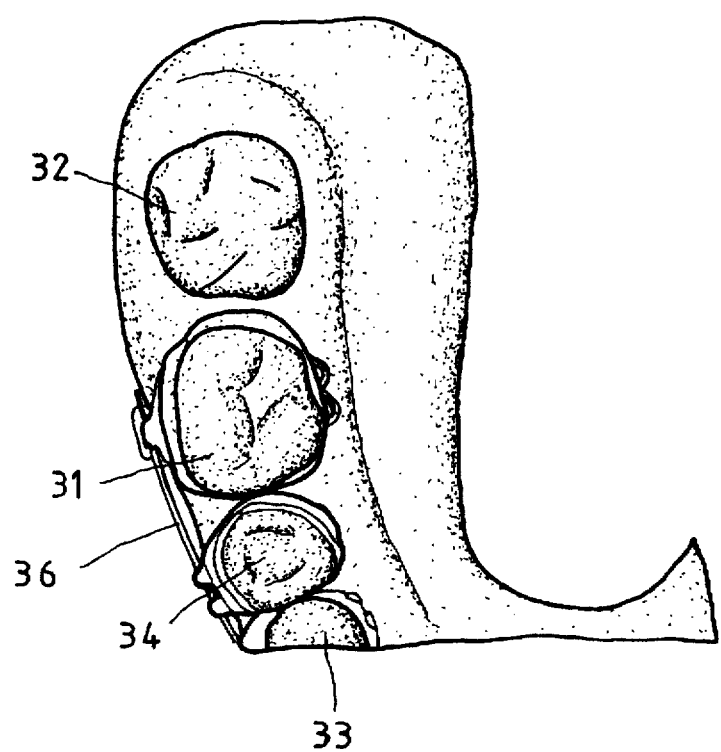
FIG. 16 illustrates the result after the molars being uprighted.
Figures 17A, 17B:
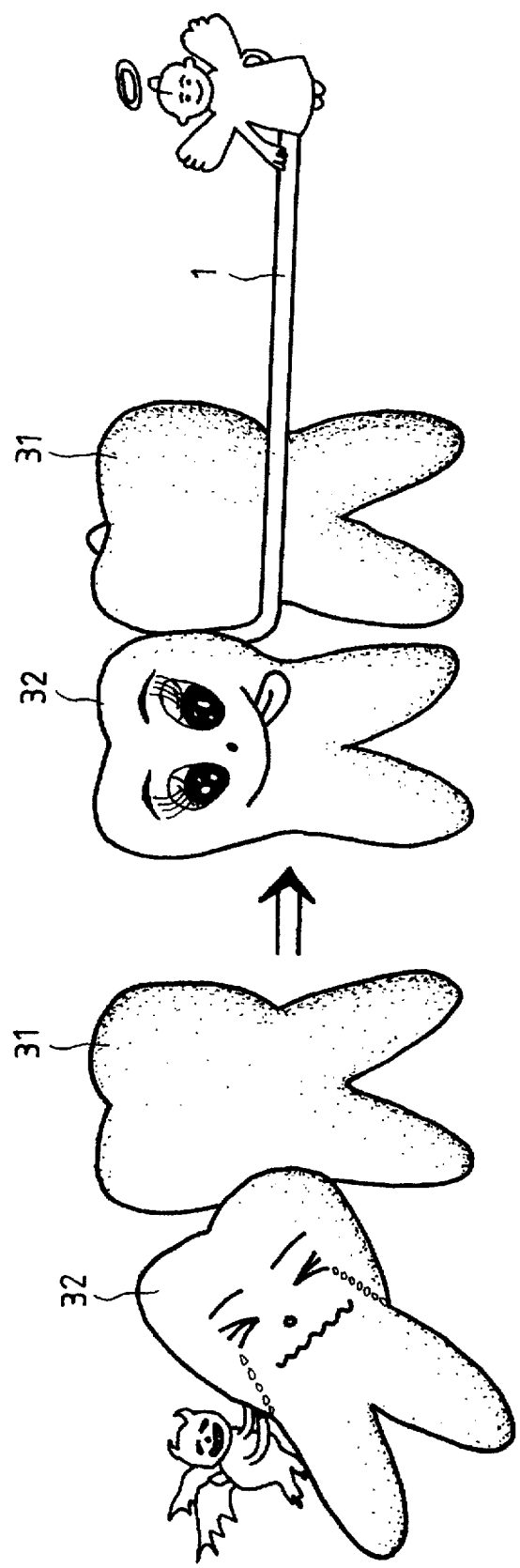
FIG. 17a and 17b illustrate the state of the impacted molar before and after orthodontic treatment respectively.

(7). Through the aforesaid orthodontic steps 1–6, the second molar 32 of a patient would have a satisfactory uprighting result in a short period (about 2 to 5 weeks) as shown in FIG. 16. Since the present invention can provide a unique, simple and quick orthodontic result, it is deemed novel. FIG. 17a illustrates the arrangement of the second molar 32 prior to orthodontic treatment, while FIG. 17b shows the arrangement thereof after orthodontic treatment; it is apparent that they are quite different from each other, and it proves that the uprighting spring of the present invention can provide a perfect orthodontic result to the second molar 32.

In order to minimize a side effect caused by a pulling force of the uprighting spring 1 between the brackets of the first molar 31 and the canine tooth 35, the steel wire 22 used is better a heavy rectangle wire of 0.018×0.025 inches. The current orthodontic material and tools include a band 29, a bracket 30 and a main wire 36, which are tied together to provide a better anchorage unit. After the second molar 32 is uprighted, the band may be bonded in place before adjusting its angle. When the uprighting spring 1 is used first time, a local anesthesia may be used to prevent the patient from feeling unwell, after a dentist becomes familiar to using the uprighting spring 1, the anesthesia may be omitted.

In brief, the long-armed type uprighting spring 1 according to the present invention has the features of novelty to improve the drawbacks of the conventional elastic ring and brass wire, which have less results and need more time to operate; the present invention can easily be formed and operated to provide effective result to a patient within two to five weeks. The present invention is designed in accordance with the first kind lever theory, and it can overcome the difficulty of bonding to the molar 31, 32. It is apparent that the present invention is deemed patentable.

I claim:

1. A long-armed type molar uprighting spring comprising:

a lingual groove rest for mounting said uprighting spring in a lingual groove of a first molar;

a loop, which extends from said lingual groove and can be fixedly mounted around a mesial side of a second molar;

a buccal bracket rest extending from said loop for resting said upright spring on a buccal bracket of the first molar;

a reactivating area, which extends from said buccal bracket rest and fits into an area between the first molar and a second premolar to provide a stronger activating function;

a lever arm, which extends from said reactivating area to provide an uprighting function in accordance with impacted condition of the second molar;

whereby said long-armed type uprighting spring is specially designed in accordance with a first kind lever theory so as to overcome the problem of poor bonding that may affect a molar; and after said uprighting spring is mounted between molars, an impacted molar will become uprighted so as to grow continuously to a precise position.

* * * * *